United States Patent
Ritter et al.

(10) Patent No.: US 9,827,360 B2
(45) Date of Patent: Nov. 28, 2017

(54) DIALYSIS MACHINE

(71) Applicant: B. BRAUN AVITUM AG, Melsungen (DE)

(72) Inventors: Kai-Uwe Ritter, Rednitzhembach (DE); Bruno Stenzel, Muenden (DE)

(73) Assignee: B. BRAUN AVITUM AG, Melsungen (DE)

( * ) Notice: Subject to any disclaimer, the term of this patent is extended or adjusted under 35 U.S.C. 154(b) by 151 days.

(21) Appl. No.: 14/850,431

(22) Filed: Sep. 10, 2015

(65) Prior Publication Data

US 2016/0077644 A1  Mar. 17, 2016

(30) Foreign Application Priority Data

Sep. 17, 2014 (DE) .................. 10 2014 113 368

(51) Int. Cl.
*A61M 1/16* (2006.01)
*A61M 1/14* (2006.01)
*G06F 3/041* (2006.01)

(52) U.S. Cl.
CPC ............ *A61M 1/1621* (2014.02); *A61M 1/14* (2013.01); *G06F 3/0412* (2013.01); *A61M 2205/505* (2013.01); *A61M 2209/08* (2013.01)

(58) Field of Classification Search
CPC .................. A61M 1/14; A61M 1/1621; A61M 2205/505; A61M 2209/08; G06F 3/0412
See application file for complete search history.

(56) References Cited

U.S. PATENT DOCUMENTS

| | | |
|---|---|---|
| 5,650,071 A | 7/1997 | Brugger et al. |
| 6,044,691 A | 4/2000 | Kenley et al. |
| 2004/0064080 A1 | 4/2004 | Cruz et al. |
| 2009/0012455 A1 | 1/2009 | Childers et al. |
| 2009/0284108 A1 | 11/2009 | Castellano et al. |
| 2010/0130920 A1 | 5/2010 | Lo et al. |
| 2012/0200214 A1 | 8/2012 | Foerger et al. |
| 2014/0252926 A1 | 9/2014 | Schaefer et al. |

FOREIGN PATENT DOCUMENTS

| | | |
|---|---|---|
| DE | 29 709 998 | 8/1997 |
| DE | 696 34 724 | 1/2006 |
| DE | 698 37 395 | 11/2007 |
| DE | 10 2011 010249 | 8/2012 |
| DE | 10 2013 102 281 | 9/2014 |
| KR | 2009 0078598 | 7/2009 |
| WO | WO 2008/117899 | 10/2008 |

OTHER PUBLICATIONS

English Translation Korean Patent Publication No. 1020090078598 A (dated Jul. 20, 2009).*
German Search Report for DE 10 2014 113 368.4 dated Apr. 29, 2015.
European Search Report (with translation) for EP 15 18 5403 dated Feb. 10, 2016.

* cited by examiner

*Primary Examiner* — John Kim

(74) *Attorney, Agent, or Firm* — RatnerPrestia

(57) ABSTRACT

A dialysis machine having a housing and a monitor is disclosed. Situated on a front side of the housing is a front door, on the top side of which a monitor housing is formed and a monitor is fastened. The monitor is situated, at least in portions, above a top side of the housing. A comparatively low, and therefore ergonomic, storage surface may be formed or situated behind the monitor on the top side of the housing.

14 Claims, 1 Drawing Sheet

DIALYSIS MACHINE

CROSS REFERENCE TO RELATED APPLICATIONS

This application claims priority to German application DE 10 2014 113 368.4 filed Sep. 17, 2014, the contents of such application being incorporated by reference herein.

FIELD OF THE INVENTION

The present invention relates to a dialysis machine and in particular to the housing of such a dialysis machine, having an integrated function/control display unit, preferably in the form of a monitor or touchscreen.

BACKGROUND OF THE INVENTION

Dialysis machines are medical devices with which the blood of a patient may be treated extracorporeally, for example when the renal function of the patient is limited. For this purpose, a dialyzer is mounted on such a dialysis machine, on the one hand the blood of the patient to be cleaned, and on the other hand a dialysate, flowing through the dialyzer, whereby certain dissolved substances (urea, for example) are transferred from the blood to the dialysate. To this end, the blood to be cleaned is led from the patient to the dialyzer, and the cleaned blood is led back to the patient, via hose lines. The fresh dialysate is likewise led to the dialyzer, and used dialysate is removed from the dialyzer, via other lines.

Dialysis machines of this type exist in the form of stationary (fixed), as well as mobile stations, wherein in particular in the latter variant, the machine housing may be moved with rollers mounted thereon. On its front side, usually above the housing, the housing of a dialysis machine has a monitor or a touchscreen on which at least the current operating data of the machine may be read, and optionally machine and/or patient data for proper operation may be entered.

It is known from the prior art to integrate the monitor into the front side or to adaptively install it on the top side of the housing.

When the monitor is integrated into the front side of the housing in a fixed manner, it is generally not possible to open the front side for maintenance purposes. For this reason, service hatches are provided at the rear side or at side areas of the machine housing. Moreover, ergonomic positioning and alignment of the monitor is difficult, since in addition to the monitor/touchscreen, other functional elements such as pumps, sensors, hose guides, etc. are situated on the front side of the machine which limit the space for mounting the monitor/touchscreen.

In the adaptive installation above the housing or on the upper housing cover, spaces result between the monitor/touchscreen and the housing, which are difficult to clean. When the monitor/touchscreen is also placed on a slewing ring as a mounting base, this interface with the housing must be laboriously sealed off, and additional EMC measures may be necessary.

DESCRIPTION OF THE RELATED ART

A dialysis machine of this type is known from the prior art, whose housing has a front door in a section of the front side of the housing, and whose monitor/touchscreen is attached above this front door in another section of the front side of the housing, below the upper housing cover/lid. The housing of the monitor/touchscreen thus has a design which is integrated into the housing of the dialysis machine or is adaptively screwed to the front side of the housing. The monitor/touchscreen therefore remains fixed to the housing above the front door, even when this door is opened, and in principle may thus be read only from the front of the machine.

A disadvantage of dialysis machines of this type is that the front side of the dialysis machine is interrupted by a joint. That is, the front side of the machine housing is divided into two sections, namely, a bottom section formed by the housing door, and a top section formed by a fixed housing wall as the support/mounting surface for control elements, displays, and the monitor/touchscreen of the dialysis machine. A joint in which dirt may collect and which is visible from the front is necessarily formed between the two sections.

However, another dialysis machine of this type is known from the prior art, whose machine housing on the front side has a housing door which extends over the entire housing side between the housing base and the housing cover. In this case, the monitor/touchscreen is screwed to the housing cover via a preferably rotatable mounting base or pedestal. The mounting base does allow the monitor/touchscreen to swivel and rotate in such a way that it is easily readable from all directions/from all sides of the machine housing. However, the mounting base takes up a large portion of the surface area of the machine cover, so that the latter is no longer available as a storage surface for various objects.

SUMMARY OF THE INVENTION

Against this background, an object of the invention is to provide a dialysis machine having a monitor/touchscreen, and a front door whose front side can be configured and manufactured to have a flat or planar design without a front joint (recess) which is difficult to clean. A preferred goal is to allow the monitor/touchscreen to be readable/operable from different sides of the machine. Lastly, a further preferred goal is to obtain a storage surface for various objects, in particular concerning the dialysis treatment, from the area provided by the top housing cover.

This object and the further goals are achieved and met by a dialysis machine having the features of the independent claim. Further advantageous embodiments of the invention are described in the dependent claims.

The basic concept of the invention lies essentially in extending the front door of the machine housing, at least in areas, beyond the upper housing cover/housing lid. The resulting extended door section, which protrudes beyond the machine housing/housing cover in a shield-/board-like manner and which therefore does not actually have a door function for closing a housing opening, is used as a mounting/installation section for the monitor/touchscreen. The monitor/touchscreen thus has the ergonomically correct position/height for good readability/operability, and may also be swiveled together with the front door so that it is also readable/operable from a side or rear direction with respect to the machine housing. In addition, since the monitor/touchscreen is mounted on the front door or integrated into same, the entire housing cover is retained as a storage surface.

Specifically, the claimed dialysis machine has a housing which has, for example, a cabinet-like main section, on the front side of which a front door is situated (hinged). The front door may cover/form the entire front side of the cabinet-like housing main section, preferably with the exception of an optionally recessed housing base. In addition, the dialysis machine has a monitor/touchscreen which is situated, at least in portions, above the main section of the housing. According to aspects of the invention, the monitor/touchscreen is fastened to the front door or is integrated into same. Thus, the entire front side, possibly with the exception of the housing base, may be designed and easily manufactured to be flat and uniform. A location/groove/recess at the front side of the dialysis machine which is difficult to clean is not present.

In particular, when the front door is fastened at one side of the housing main section with suitable hinges or strap hinges, the front door may be swiveled out over at least 90°, preferably over approximately 180°. The monitor/touchscreen may thus also be read by a person who is at the rear side of the dialysis machine and is carrying out maintenance activities, for example.

In one refinement which is technically simple in terms of the device, a monitor housing or monitor storage compartment is formed in one piece with the front door. In this case, the rear side of the monitor/touchscreen is protectively covered by the front door, whereas the monitor/touchscreen fits in flush alignment, or with only a slight projection, against the front surface of the front door.

When the front door is made of sheet metal, it may be easily bent/folded at its edge to form stabilizing webs or strips. Thus, in the closed state the front door may encompass the housing/the main section thereof from the outside, so that the joint between the door and the housing is not visible from the front. The visual appearance of the dialysis machine is improved in this way.

To avoid dirt-collecting corners, it is preferred for the monitor housing and the front door to have approximately the same width.

The entire monitor housing or the monitor storage compartment preferably extends above the top side of the main section of the housing, i.e., above the upper housing cover. Thus, if the front door is closed in such a way that its front panel rests against the housing, the monitor/the monitor storage compartment slightly overlaps the housing cover corresponding to the depth of the monitor housing. A joint is thus formed between the front door and the housing which extends uniformly on one level around the entire housing without corners being formed.

In one particularly preferred refinement of the dialysis machine according to aspects of the invention, an essentially flat storage surface, for example for a container with dialysis accessories, is formed or situated on a top side of the main section of the housing (housing cover). This storage surface is situated behind the monitor/touchscreen, and therefore at a lower level than storage surfaces according to the prior art, thus improving the ergonomics. When the front door is opened and the monitor/touchscreen is thus swiveled away, the storage surface is particularly easily accessible, even from the front side.

In a first variant according to aspects of the invention, the storage surface extends essentially over the entire area of the housing top side/housing cover. In a second variant according to aspects of the invention, the storage surface has a border which prevents, for example, the container with dialysis accessories from falling down.

For aesthetic reasons, an upper frame surface of the border may be oriented approximately perpendicularly with respect to the monitor or the front door. Thus, when the monitor or the front door, for example, is oriented vertically, the upper frame surface of the border is oriented horizontally. For ergonomic reasons, it is preferred when the monitor and/or the front door have/has a non-vertical inclination so that actuating and reading units mounted thereon are more accessible. For esthetic reasons, the inclinations of the monitor and of the front door should be approximately the same. In the above-mentioned second variant of the storage surface, for esthetic reasons it is preferred that the upper frame surface of the border has the same inclination with respect to the horizontal as the monitor and/or the front door have/has with respect to the vertical. This also ensures that dripping water, for example, runs to the rear, away from the monitor and the control elements, and does not collect in the joint between the front door and the housing cover. Any damage to the paint, for example due to the container with dialysis accessories which are deposited on the storage surface, is additionally concealed by the inclined upper frame surface.

In one preferred embodiment of the second variant, the border extends in the area of the monitor or monitor housing and at both sides of the top side. The border thus has a U shape and is open at a rear side of the main section of the housing.

Due to the bent stabilizing webs/strips, lateral joints between the main section of the housing and the front door thereof preferably are situated at a distance of 6 cm maximum, in particular approximately 4 cm, from the front side of the main section.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
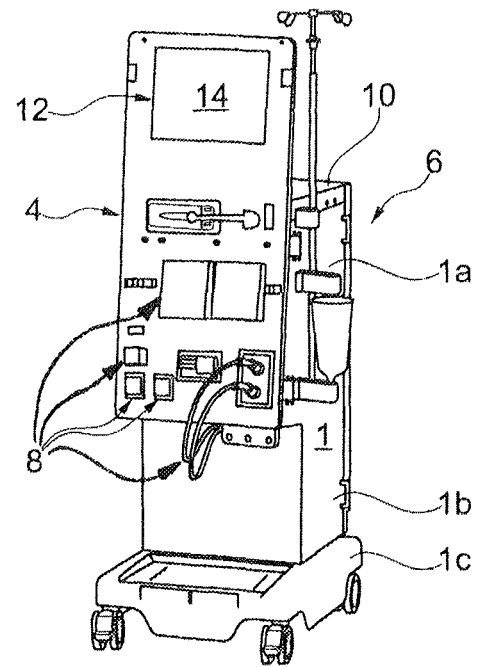
FIG. 1 shows a preferred exemplary embodiment of the dialysis machine according to aspects of the invention in a perspective front view.

FIG. 1 shows a perspective front view of the dialysis machine according to aspects of the invention. The dialysis machine has a housing 1 with a cabinet-like, approximately cuboidal main section 1a which rests on a housing base 1b which is recessed with respect to the front side of the main section 1a, and which in turn rests on a platform 1c. Three or four rollers 2 are mounted on the bottom side of the platform 1c, via which the dialysis machine may be moved.

A front door 4 is provided on a front side of the main section 1a, and in the present case covers the entire area of the front side of the main section 1a, while a rear door 6 is provided on a rear side of the housing 1. The front door 4 is inclined by several degrees with respect to the vertical so that functional elements 8, for example pumps, sensors, hose guides, etc., situated on the front door correspondingly face slightly upwardly.

In the present exemplary embodiment, the front door 4 preferably protrudes by approximately one-third of its height beyond a top side/housing cover 10 of the main section 1a of the housing 1. In this section, the front door 4 forms a monitor/touchscreen housing or storage compartment 12 in which a monitor or touchscreen 14 (referred to hereinafter only as "monitor") is accommodated. The monitor 14 together with the front door 4 and the functional elements 8 situated thereon is inclined by several degrees with respect to the vertical, and is thus optimally directed at the viewing height of an operator of average height.

According to FIG. 1, the front door 4 is pivotably fastened to a side surface of the housing main section 1a, and may therefore be swiveled out from its closed position by at least 180°, as described in greater detail below.

Figure 2:
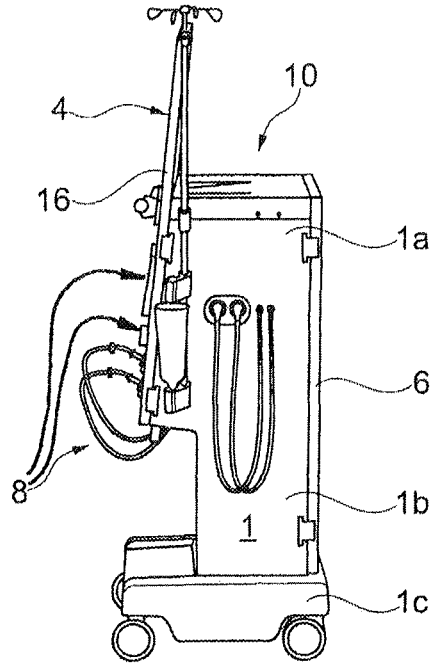
FIG. 2 shows the preferred exemplary embodiment of the dialysis machine according to aspects of the invention in a side view.

FIG. 2 shows the dialysis machine according to FIG. 1 in a side view. The front door 4 and the monitor housing 12 are made of one piece of sheet metal, and the front door has a border or folded edge 16, approximately 4 cm wide, that is formed by bending the sheet metal to the rear by 90°. Since the monitor housing/storage compartment 12 has a depth of approximately 4 cm and the width of the monitor housing/storage compartment 12 corresponds to that of the front door 4, the monitor housing 12 in terms of shape and manufacturing is optimally integrated into the front door 4. The entire front control panel formed on the front door 4 is therefore optimally flat, uniform, and free of joints, in a manner of speaking.

Figure 3:
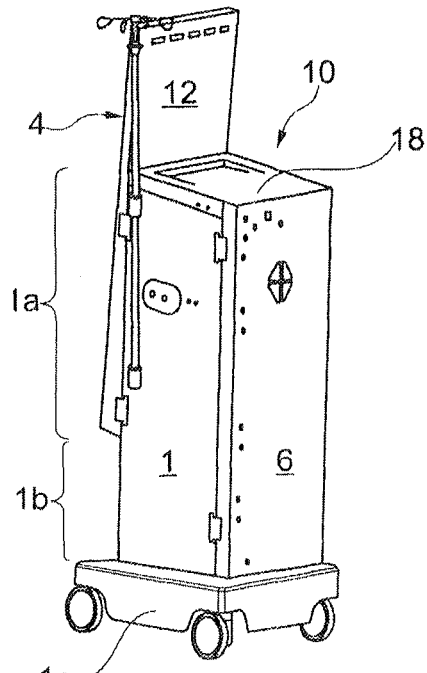
FIG. 3 shows the preferred exemplary embodiment of the dialysis machine according to aspects of the invention in a perspective rear view.

FIG. 3 shows the dialysis machine of the preceding figures in a perspective rear view. When, for example, a person is working on the dialysis machine via the rear door 6, he/she can swivel the front door 4 by approximately 180°, according to the above description, and read the monitor 14 (see FIG. 1) from the rear direction. Since the front door 4 is fastened to the main section 1a at an angle, the monitor 14 in the swiveled-out state of the front door 4 is inclined slightly downwardly, and may thus be easily read by a person who is bent over or kneeling for maintenance purposes.

Situated on the top side/housing cover 10 of the main section 1a of the housing 1 is an essentially flat storage surface 18 which is situated approximately at the level of the lower edge of the monitor 14, and thus at an optimal depth.

Figure 4:
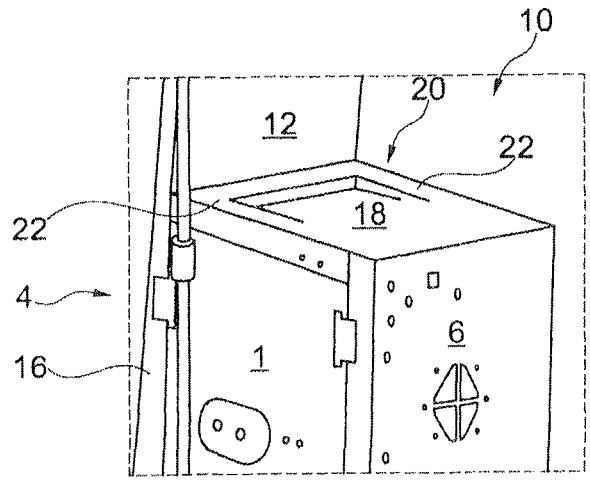
FIG. 4 shows a detail from FIG. 3.

FIG. 4 shows the top side 10 of the main section 1a of the housing 1. The storage surface 18 formed there is provided with a three-sided border 20. This border has a certain width, so that a strip-shaped frame surface 22 is formed on the top side of the border 20. For esthetic reasons, the frame surface is inclined by the same angle with respect to the horizontal as the front door 4 is inclined with respect to the vertical. For technical reasons, the inclined position is provided to keep water, preferably dripping water, away from the front side of the housing 1.

A slip-resistant mat is provided on the storage surface 18 to prevent objects from falling down via the rear open side.

A dialysis machine having a housing and a monitor is disclosed. Situated on a front side of the housing is a front door, on the top side of which a monitor housing is formed and a monitor is fastened. The monitor is situated, at least in portions, above a top side of the housing. A comparatively low, and therefore ergonomic, storage surface may be formed or situated behind the monitor on the top side of the housing.

The invention claimed is:

1. A dialysis machine comprising:
   a housing having a main section with a front side and a side surface;
   a hinge having a first side and a second side, the first side connected to the side surface;
   a front door situated on the front side of the main section, connected to the second side of the hinge, and pivotally fastened at an incline in a vertical dimension to the main section by the hinge, at least a portion of the front door protruding upwardly in the vertical dimension beyond the main section of the housing, wherein the front door is configured to swivel outward with respect to the vertical dimension; and
   a monitor or touchscreen situated on the front door in the upwardly protruding portion, at least a portion of the monitor or touchscreen positioned above the main section.

2. The dialysis machine according to claim 1, wherein the front door is pivotable at least over 90°.

3. The dialysis machine according to claim 1, wherein the front door is pivotable at least over 180°.

4. The dialysis machine according to claim 1, further comprising:
   a monitor housing or storage compartment for the monitor or touchscreen, at least a portion of the monitor housing or storage compartment formed in one piece with the front door above the main section of the housing.

5. The dialysis machine according to claim 4, wherein the monitor housing or storage compartment and the front door each have a width such that the front door forms a strip-shaped edge or frame around the monitor housing or storage compartment.

6. The dialysis machine according to claim 1, wherein the front door is made of sheet metal, which at the door periphery is folded down to form a rim whose width corresponds approximately to the depth of the monitor or touchscreen or a housing or storage compartment for the monitor or touchscreen.

7. The dialysis machine according to claim 1, wherein an essentially flat storage surface is formed or situated on a top side or housing cover of the main section, wherein the surface area of the storage surface corresponds to the dimensions of the main section.

8. The dialysis machine according to claim 7, wherein the storage surface extends over the entire width of the top side.

9. The dialysis machine according to claim 7, wherein the storage surface has a border.

10. The dialysis machine according to claim 9, wherein an upper frame surface of the border is oriented perpendicularly with respect to at least one of the monitor or touchscreen or the front door.

11. The dialysis machine according to claim 9, wherein the border extends in the area of the monitor or touchscreen and at both sides of the top side or housing cover of the main section.

12. The dialysis machine according to claim 1, wherein at least one of the monitor or touchscreen or the front door has a non-vertical inclination.

13. The dialysis machine according to claim 12, wherein the inclinations of the monitor or touchscreen and the front door are approximately the same.

14. The dialysis machine according to claim 1, wherein the monitor or touchscreen is situated in an integrated manner on the front door in the upwardly protruding front door portion.

* * * * *